(12) United States Patent
Landes et al.

(10) Patent No.: US 12,168,080 B2
(45) Date of Patent: Dec. 17, 2024

(54) ARRANGEMENT FOR THE CONTAMINATION-FREE INTRODUCTION OF A STERILE OBJECT FROM A CONTAINER INTO A CONTAINMENT AND METHOD THEREFOR

(71) Applicant: Pharma Integration S.R.L., Siena (IT)

(72) Inventors: Robert Landes, Bad Säckingen (DE); Mathieu Müller, Sierentz (FR); Kathrin Sprecher, Basel (CH); Mike Zeller, Wahlen (CH)

(73) Assignee: Pharma Integration S.R.L. (IT)

( * ) Notice: Subject to any disclaimer, the term of this patent is extended or adjusted under 35 U.S.C. 154(b) by 592 days.

(21) Appl. No.: 17/260,776

(22) PCT Filed: Jul. 17, 2019

(86) PCT No.: PCT/IB2019/000620
§ 371 (c)(1),
(2) Date: Jan. 15, 2021

(87) PCT Pub. No.: WO2020/016645
PCT Pub. Date: Jan. 23, 2020

(65) Prior Publication Data
US 2021/0275709 A1    Sep. 9, 2021

(30) Foreign Application Priority Data

Jul. 18, 2018  (CH) ........................ 888/18

(51) Int. Cl.
*A61L 2/00* (2006.01)
*A61L 2/26* (2006.01)
*B25J 21/00* (2006.01)

(52) U.S. Cl.
CPC .............. *A61L 2/26* (2013.01); *A61L 2/0029* (2013.01); *A61L 2/0094* (2013.01);
(Continued)

(58) Field of Classification Search
CPC .............. B25J 21/005; A61L 2202/121; A61L 2202/122; A61L 2202/23
See application file for complete search history.

(56) References Cited

U.S. PATENT DOCUMENTS

| | | |
|---|---|---|
| 5,226,781 A | 7/1993 | Glachet et al. |
| 5,421,626 A | 6/1995 | Glachet |
| (Continued) | | |

FOREIGN PATENT DOCUMENTS

| | | |
|---|---|---|
| CN | 1117605 A | 2/1996 |
| CN | 102821858 A | 12/2012 |
| (Continued) | | |

OTHER PUBLICATIONS

EP 1510227 A1 Translation.*
(Continued)

*Primary Examiner* — Kevin Joyner
*Assistant Examiner* — Changru Chen
(74) *Attorney, Agent, or Firm* — Endurance Law Group PLC

(57) ABSTRACT

The arrangement for contamination-free introduction of a sterile object from a vessel, closed by means of a semipermeable cover, into a working chamber, surrounded by a wall, of a containment comprising a portal unit having an access flange arranged in the wall and forming a passage into the working chamber, and a door which sealingly closes the passage and which, in order to be opened, can be moved into the working chamber. The arrangement comprises a vessel receptacle having a repository for holding a vessel, an opening for introducing the vessel into the repository, and a flange for interacting with the access flange. A decontamination unit designed to, when the door is closed, the vessel receptacle is docked to the access flange and the vessel is stored in the vessel receptacle, decontaminate an outer (Continued)

Figure 1A:
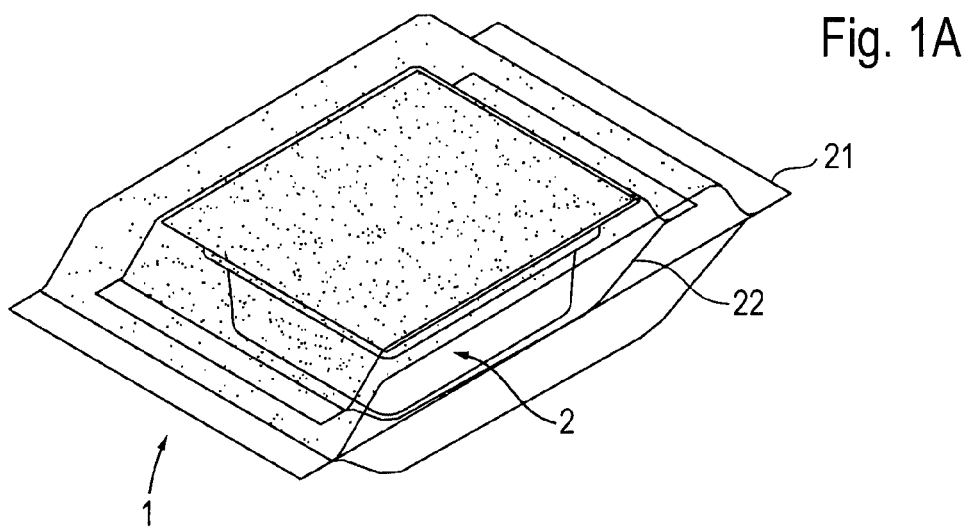

surface of the cover. Based on this arrangement, a method for introduction is also disclosed.

9 Claims, 19 Drawing Sheets

(52) U.S. Cl.
CPC ....... B25J 21/005 (2013.01); *A61L 2202/121* (2013.01); *A61L 2202/122* (2013.01); *A61L 2202/23* (2013.01)

(56) References Cited

U.S. PATENT DOCUMENTS

| | | | |
|---|---|---|---|
| 5,425,400 | A | 6/1995 | Szatmary |
| 5,447,699 | A * | 9/1995 | Papciak ................ B65B 55/027 |
| | | | 422/294 |
| 5,460,439 | A | 10/1995 | Jennrich et al. |
| 5,735,609 | A | 4/1998 | Norton |
| 5,892,200 | A | 4/1999 | Kendall et al. |
| 5,934,859 | A | 8/1999 | Goetzelmann |
| 6,030,578 | A | 2/2000 | McDonald |
| 6,749,808 | B1 | 6/2004 | Huynen et al. |
| 6,779,567 | B1 | 8/2004 | Szatmary |
| 2004/0228759 | A1 | 11/2004 | Frost |
| 2008/0072996 | A1 | 3/2008 | Py |
| 2011/0024419 | A1 | 2/2011 | Gabel et al. |
| 2015/0197387 | A1 | 7/2015 | Yeager et al. |
| 2016/0200461 | A1 | 7/2016 | Broadbent et al. |
| 2017/0247132 | A1 | 8/2017 | Deutschle et al. |
| 2017/0291774 | A1 | 10/2017 | Procyshyn et al. |
| 2018/0290136 | A1 | 10/2018 | Koike et al. |
| 2019/0269809 | A1 * | 9/2019 | Grajcar ................... A61L 2/202 |

FOREIGN PATENT DOCUMENTS

| | | | | |
|---|---|---|---|---|
| CN | 106999616 | A | 8/2017 | |
| EP | 1109173 | A1 | 6/2001 | |
| EP | 1510227 | A1 * | 3/2005 | ............... A61L 2/07 |
| EP | 3263297 | A1 | 1/2018 | |
| EP | 3335844 | A1 | 6/2018 | |
| JP | 2000357727 | A | 12/2000 | |
| JP | 2011160672 | A | 8/2011 | |
| JP | 2016086709 | A | 5/2016 | |
| WO | 9422715 | A1 | 10/1994 | |
| WO | 9621615 | A2 | 7/1996 | |
| WO | 9833719 | A1 | 8/1998 | |
| WO | WO-03022313 | A2 * | 3/2003 | ............... A61L 2/04 |
| WO | 2010/145042 | A1 | 12/2010 | |
| WO | 2012153092 | A1 | 11/2012 | |
| WO | WO-2013022785 | A2 * | 2/2013 | ............. A61L 2/202 |
| WO | 2013166379 | A1 | 11/2013 | |
| WO | WO-2017129362 | A2 * | 8/2017 | ............... A61L 2/07 |
| WO | 2018019782 | A1 | 2/2018 | |
| WO | WO-2018019785 | A1 * | 2/2018 | ......... B65B 69/0008 |

OTHER PUBLICATIONS

International Search Report of the International Searching Authority, along with an English translation, mailed on Jan. 23, 2020, issued in connection with International Application No. PCT/IB2019/000620 (5 pages).

Written Opinion of the International Searching Authority mailed on Jan. 23, 2020, issued in connection with International Application No. PCT/IB2019/000620 (9 pages).

H.-J. Bässler and F. Lehman, "Containment Technology Progess in the Pharmaceutical and Food Process Industry," Springer-Verlag, Berlin, Heidelberg, Jan. 1, 2013, pp. 88-104 (15 pages).

Baessler et al., "Containment Technology", 978-3-642-39292-4, Oct. 1, 2013, Berlin-Heidelberg, 176 pages.

Machine translation of New arguments from the EPO Opponent for European Patent No. EP3823770, dated Apr. 16, 2024, 14 pages.

Machine translation of Opposition Notice for European Patent No. EP3823770B1, dated Mar. 21, 2023, 27 pages.

Machine translation of Preliminary Opinion of the EPO for European Patent No. EP3823770, dated Apr. 29, 2024, 11 pages.

Millipore Biopharmaceutical Division 1, "Operating and Maintenance Manual SafePass® Sterile Transfer System", retrieved from https://www.fortigraphics.com/Portfolio/Millipore/SafePass.htm, 92 pages.

Thorogood, "A history of isolator and containment technology Part 4: Transfer devices", Clean Air and Containment Review, Issue 21, Jan. 2015, 5 pages.

* cited by examiner

ARRANGEMENT FOR THE CONTAMINATION-FREE INTRODUCTION OF A STERILE OBJECT FROM A CONTAINER INTO A CONTAINMENT AND METHOD THEREFOR

RELATED APPLICATIONS

This application is a U.S. National Phase Application under 35 U.S.C. 371 of International Application No. PCT/IB2019/000620 filed Jul. 17, 2019, which claims the benefit of Swiss Patent Application No. 00888/18 filed on Jul. 18, 2018. The disclosures of these applications are incorporated herein by reference in their entireties.

FIELD OF USE OF THE INVENTION

The invention relates to an arrangement and to a method for the contamination-free introduction of a sterilized object from a vessel, which has been closed by means of a cover, into a working chamber, which is surrounded by a wall, of a containment. Typically, in the laboratory technology field, the pharmaceutical industry or the biotechnology field, such vessels have the form of trough-shaped tubs, and the objects are nests with a raster of depression-like receiving contours for the storage of containers, for example vials or syringes.

PRIOR ART

Special devices, as disclosed for example in WO 2010/145 042 A1, are required not only for the safe discharge of objects from a containment but also for the introduction of objects into a containment. During the introduction, it is firstly necessary to avoid opening of the containment to the outside, in order that both the defined clean-room state in the containment is maintained and also no hazardous particles escape from the containment to the outside. Furthermore, during the introduction of sterilized objects, these must be protected such that, during the introduction, the objects themselves are not exposed to any contaminants from the surroundings.

In the monograph by H.-J. Bassler and F. Lehman: Containment Technology, Springer-Verlag, Berlin, Heidelberg, 2013, pages 88 et seq., a transfer system (Rapid Transfer Port—RTP) which satisfies the abovementioned conditions is described. Here, in the wall of the containment, there is provided a port, normally in the form of a circular window, which is bordered by a sealed inner flange. In the initial situation, said inner flange is closed by means of a door element which can be opened into the interior of the containment and which is sealed against the inner flange. The object to be transferred into the containment—for example a sterile pharmaceutical product—is enclosed in an externally sealed capsule which is initially detached from the containment and on which the mouth is bordered by a sealed outer flange on which there is seated a cover which imparts a sealing closing action. In a first transfer step, the capsule is docked to the assembly composed of inner flange and door element, such that the inner flange and the outer flange, and also the door element and the cover, are sealingly locked together, and the door element, together with the cover, surrounds the two unsterile outer surfaces thereof. In the next transfer step, the assembly composed of door element and cover is moved from the assembly of the two flanges into the interior of the containment, such that the mouth of the capsule is now open, and the sterile object can be moved from the container into the interior of the containment.

The previous handling process is equivalent, in principle, if the product that is to be introduced into the containment is a closed vessel with a sterile object present therein. Such a configuration arises if the vessel has the form of what is known in the medical technology field as a tub, which is sealed for example by means of a cover composed of nonwoven fabrics such as Tyvek®, and the sterile object, which has the form of a so-called nest in which a multiplicity of vials or medical syringes are deposited, is situated in the vessel. In the case of the above-described transfer system being used for the above-defined vessel (sealed tub with inner nest, populated for example with vials), two alternative methods are available. In the case of the first method, the vessel with its content would also have to be externally decontaminated before being introduced into the capsule, or the vessel is decontaminated in the capsule, in order, after the transfer into the containment, for the sterile object to be unpacked therein. The second method would be for the object to be unpacked from the vessel under sterile conditions, introduced in this form into the capsule, and ultimately transferred into the containment. Another alternative is for the object to be unpacked in an unprotected manner and then decontaminated in the capsule and ultimately transferred into the containment. A further method is for the vessel to be removed from the enclosures under controlled conditions, and subsequently, in order to clear potential contamination in the interim, the vessel with the cover that closes it is irradiated on all sides in an E-beam installation. The transfer into the containment is then performed, the cover is removed, the object is removed, and the containers stored in magazine form therein are separated out.

The above solutions are cumbersome in terms of handling and, for the unpacking of the object, require increased outlay in terms of apparatus in the containment and/or outside the latter.

OBJECT OF THE INVENTION

In view of the hitherto incomplete solutions, the object on which the invention is based is that of creating an arrangement which is designed for the contamination-free introduction of a sterile object from a vessel into a containment, and proposing a method utilizing the arrangement created. Here, it is the aim to make the handling as simple as possible, while ensuring compliance with cleanliness requirements and optimized outlay in terms of apparatus. Specifically, it is an aim to introduce as far as possible only those materials and items of equipment into the containment which are required for the immediate processing operation, and at the same time to minimize the degree of decontamination required.

OVERVIEW OF THE INVENTION

The arrangement for the contamination-free introduction of a sterile object from a vessel, which has been closed by means of a semipermeable cover, into a working chamber, which is surrounded by a wall, of a containment comprises:
  a) a portal unit having:
    aa) an access flange which is arranged in the wall and which forms a passage from the outside into the working chamber; and ab) a door which sealingly closes the passage and which, in order to be opened, can be moved into the working chamber; and
b) a vessel receptacle having:
ba) a repository for holding a vessel that has been introduced into the vessel receptacle;
bb) an opening for the introduction of the vessel into the repository; and
bc) a flange for interacting with the access flange.

A decontamination unit is designed to, when the door has been closed, the vessel receptacle has been docked to the access flange and the vessel has been stored in the vessel receptacle, decontaminate an outer surface, facing toward the door, of the cover.

Below, specific embodiments of the invention will be defined: the door, in a closed position, is attached in a sealed manner to the access flange from the side of the working chamber, and the access flange borders an intermediate space which is situated in the passage. The cover of the vessel which has been placed in the vessel receptacle is sealed between the flange and the access flange when the vessel receptacle has been pivoted into abutment against the access flange.

The decontamination unit, with a direction of action into the passage, is installed directly on the door or laterally with respect to a portal unit which has the door and the access flange. The decontamination unit is a radiation source, for example UVC, UV, E-beam or pulsed light, or is a fumigation device, for example for atomizing an $H_2O_2$ solution. The decontamination unit is furthermore utilizable for decontamination of the outwardly facing surface of the door, of the intermediate space and of that surface of the access flange which faces toward the intermediate space.

A transfer apparatus which is equipped, in the working chamber, with a tool head is designed to, when the door has been opened, the vessel receptacle has been docked to the access flange and the vessel has been stored in the vessel receptacle:
a) detach the decontaminated part of the cover from the vessel and move it into the working chamber;
b) move an inlay, which is optionally present in the vessel and which is situated above the object, into the working chamber; and
c) move the object resting in the vessel situated in the vessel receptacle from said vessel into the working chamber.

In the case of use of the arrangement in the laboratory technology field, the pharmaceutical industry or the biotechnology field:
a) the vessel has the form of a trough-shaped tub; and
b) the object has the form of a nest with a raster of depression-like receiving contours for the storage of containers, for example vials or syringes.

The arrangement is assigned an input station with an air stream flowing through a filter, which stream is intended for releasing the vessels from packages provided with, for example bag-like, enclosures and for providing the vessels, under controlled clean-room conditions, before these are placed into the vessel receptacle.

The cover which closes the vessel, and which is for example composed of nonwoven fabric such as Tyvek®, maintains the sterile state of the object, situated in the interior space of the vessel, with the containers. The cover which closes the vessel is preferably sealed against a vessel edge of the vessel.

The method for the contamination-free introduction of a sterile object from a vessel into a containment using the abovementioned arrangement comprises the following sequence of process phases:
a) removing the vessel, which has been closed by means of a cover and which contains an object, from enclosures under controlled clean-room conditions at an input station;
b) providing the respectively individual vessel, which has been closed by means of a cover and which has the sterile object stored therein, for contamination-free introduction into a working chamber of a containment; here:
the passage to the working chamber is outwardly open but, into the containment, is closed by the door, the decontamination unit is inactive, the repository of the vessel receptacle is open and empty, and the vessel receptacle is detached from the portal unit;
c) placing the provided individual vessel into the repository; here:
it remains the case that the passage is outwardly open but, into the containment, is closed by the door, the decontamination unit is inactive and the vessel receptacle is detached from the portal unit, but now the repository is filled with a vessel;
d) moving the vessel receptacle into abutment against the portal unit; here:
the access flange of the portal unit and the flange are sealed against one another;
furthermore, the passage into the containment is closed by the door, the decontamination unit is inactive and the repository is filled with a vessel; and
the passage is also outwardly closed, specifically by the vessel receptacle docked in a sealed manner to the portal unit;
e) activating the decontamination unit or bringing the latter into a state of action; here:
it remains the case that the access flange of the portal unit and the flange are sealed against one another, the passage into the containment is closed by the door, the repository is filled with a vessel, and the passage is also outwardly closed, specifically by the vessel receptacle docked in a sealed manner to the portal unit; and now
the outer surface, exposed to the door, of the cover and the intermediate space and all surfaces facing toward this are made sterile;
f) deactivating the decontamination unit or bringing the latter out of a state of action, and opening the door; here:
it remains the case that the access flange of the portal unit and the flange are sealed against one another, the repository is filled with a vessel, the passage is outwardly closed, specifically by the vessel receptacle docked in a sealed manner to the portal unit, and the outer surface of the cover, the intermediate space and all surfaces facing toward this are sterile; and now
the passage into the containment is open;
g) cutting open the cover of the vessel; here:
it remains the case that the access flange of the portal unit and the flange are sealed against one another, the repository is filled with a vessel, the passage is outwardly closed, specifically by the vessel receptacle docked in a sealed manner to the portal unit, the outer surface of the cover, the intermediate space and all surfaces facing toward this are sterile, and the passage into the containment is open; and now the access to the object situated in the vessel is open;

h) removing the object from the vessel and transferring the object with the containers stored therein into the working chamber of the containment for further processing; here:

it remains the case that the access flange of the portal unit and the flange are sealed against one another, the passage is outwardly closed, specifically by the vessel receptacle docked in a sealed manner to the portal unit, and the passage into the containment is open; and now the repository is now filled only with the empty vessel; and i) returning the arrangement into the starting phase, that is to say moving the door into the closed position, which is thus sealed against the access flange again, pivoting the vessel receptacle away from the access flange, and removing the empty vessel from the repository.

Special process phases will be mentioned below: after the vessel receptacle with the vessel that has been placed in the repository has been moved into abutment against the portal unit and before the decontamination unit is activated or brought into its state of action, the object is subjected to an integrity test in order to identify whether the content of the vessel satisfies the cleanliness requirement. If the integrity test yields a negative result, the vessel receptacle is pivoted away from the portal unit in order for the, in effect, defective vessel to be removed from the repository.

The cutting-open of the cover of the vessel, the removal of the object from the vessel and the transfer of the object with the containers stored therein into the working chamber of the containment are performed by means of the transfer apparatus positioned in the working chamber.

A cut-away part of the cover is moved into the working chamber by means of the transfer apparatus positioned in the working chamber.

The individual vessel which has been closed by means of the cover is, together with its sterile content, specifically the object stored in the vessel and the containers accommodated in said object, provided with at least one enclosure and thus, in the delivered state, forms a package.

The provision of the individual vessel before it is placed into the vessel receptacle is performed, in an input station belonging to the arrangement, as a release of the vessel from the respective package under controlled clean-room conditions.

BRIEF DESCRIPTION OF THE APPENDED DRAWINGS

Figure 1B:
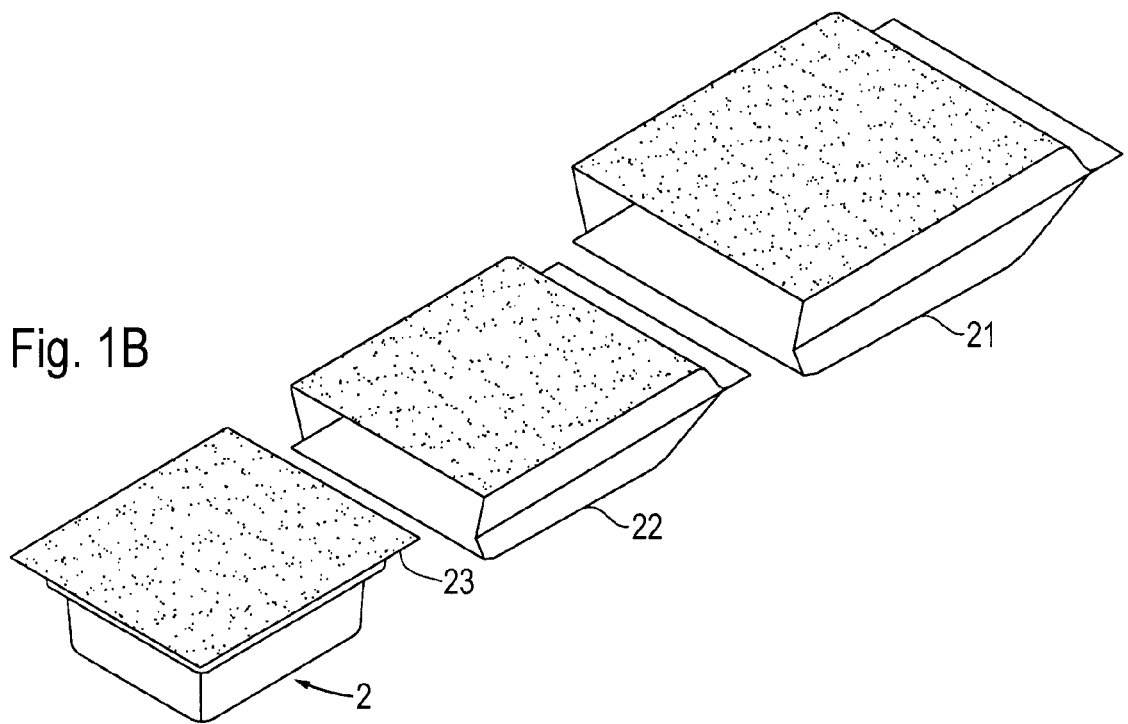
Figure 1D:
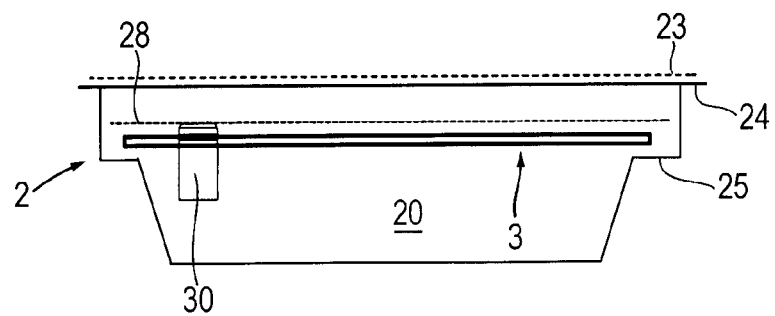
Figure 1C:
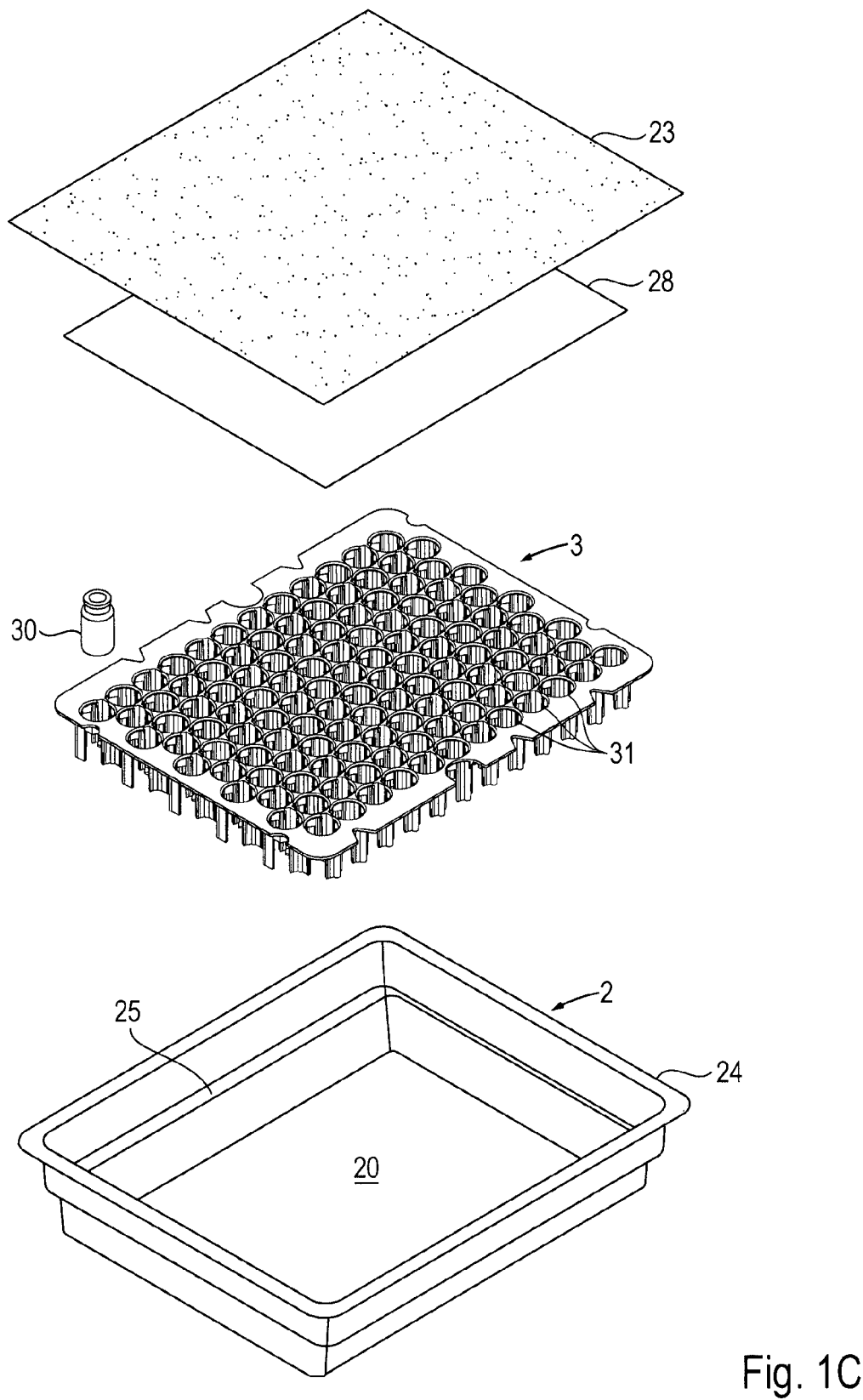
Figure 2A:
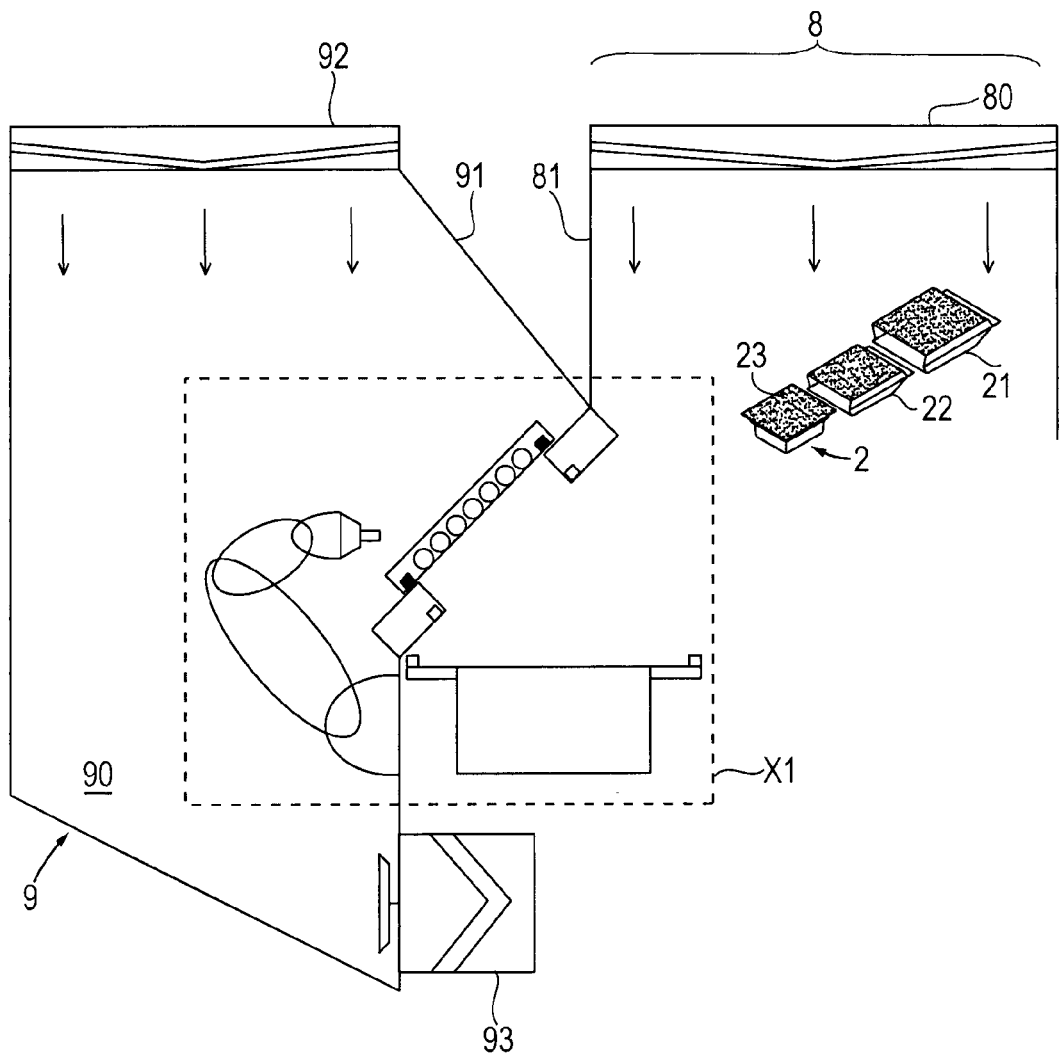
Figure 2B:
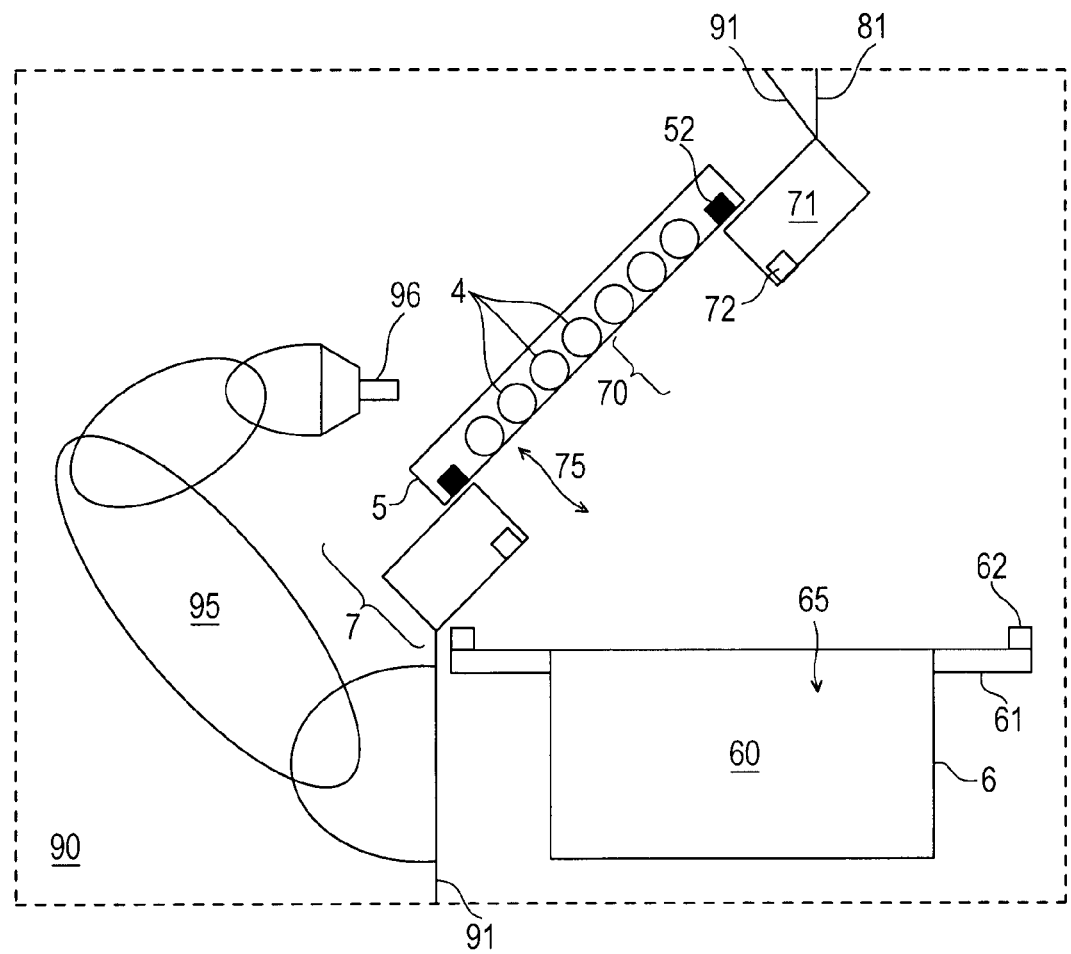
Figure 3:
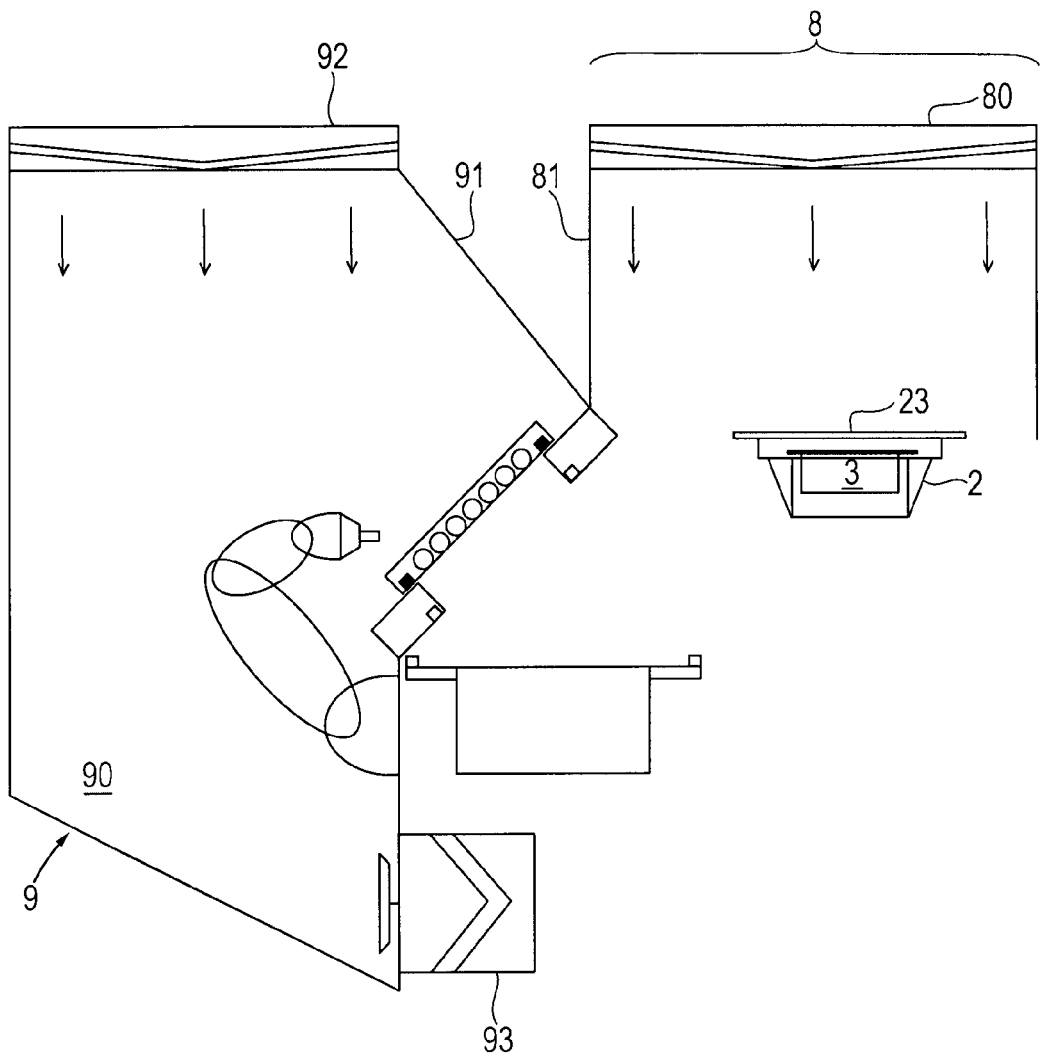
Figure 4A:
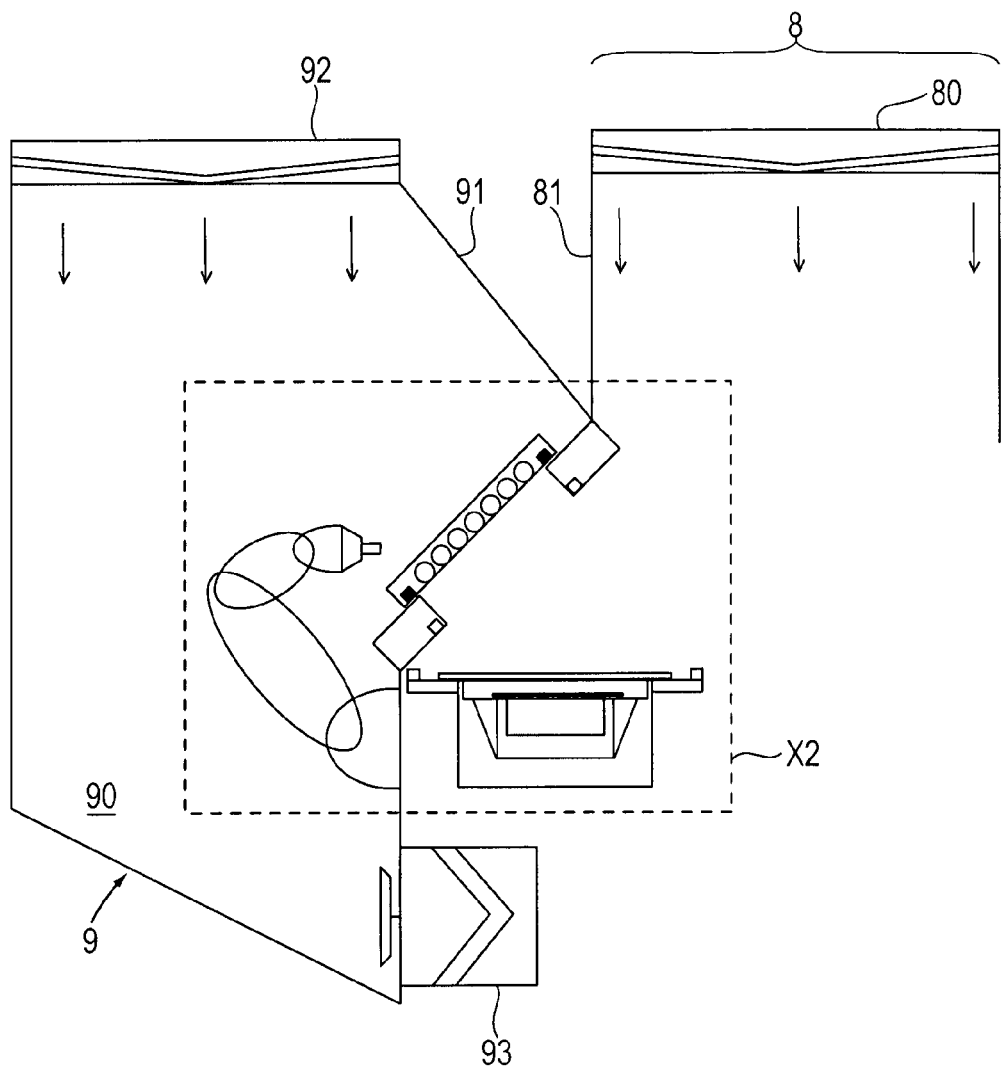
Figure 4B:
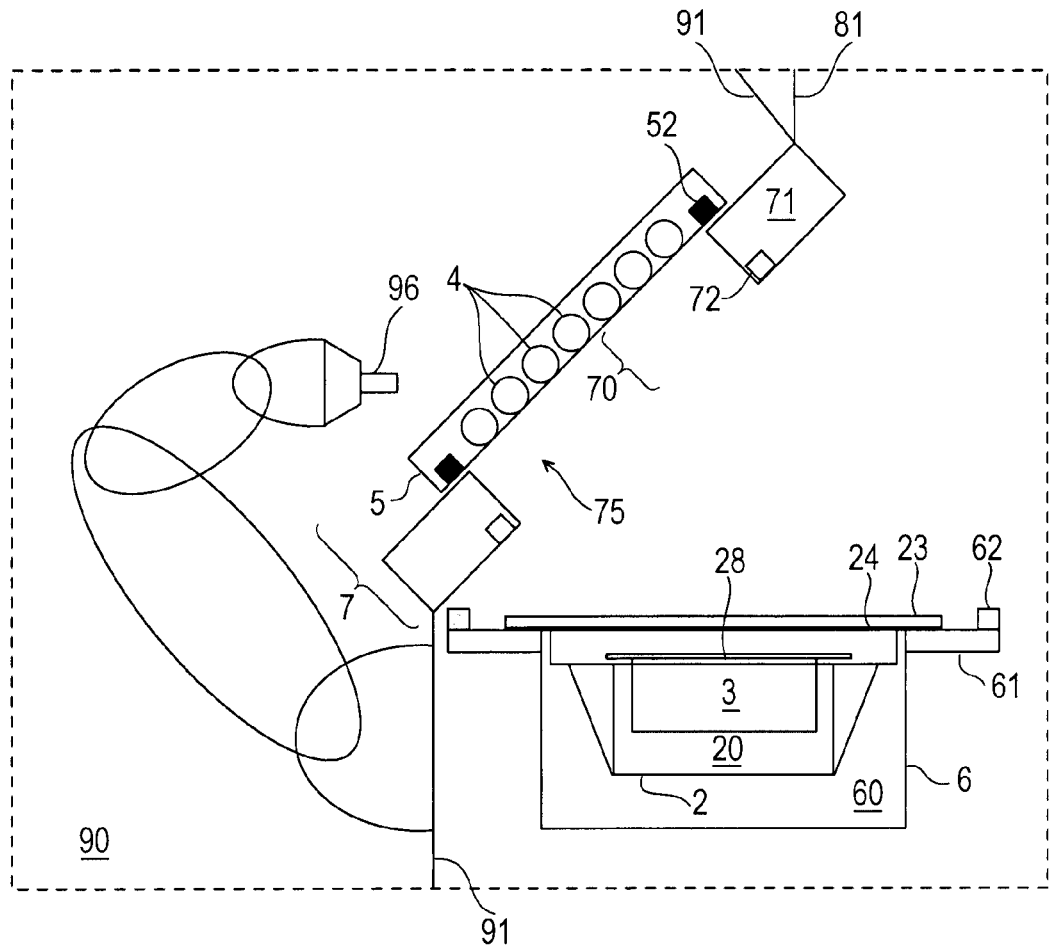
Figure 5A:
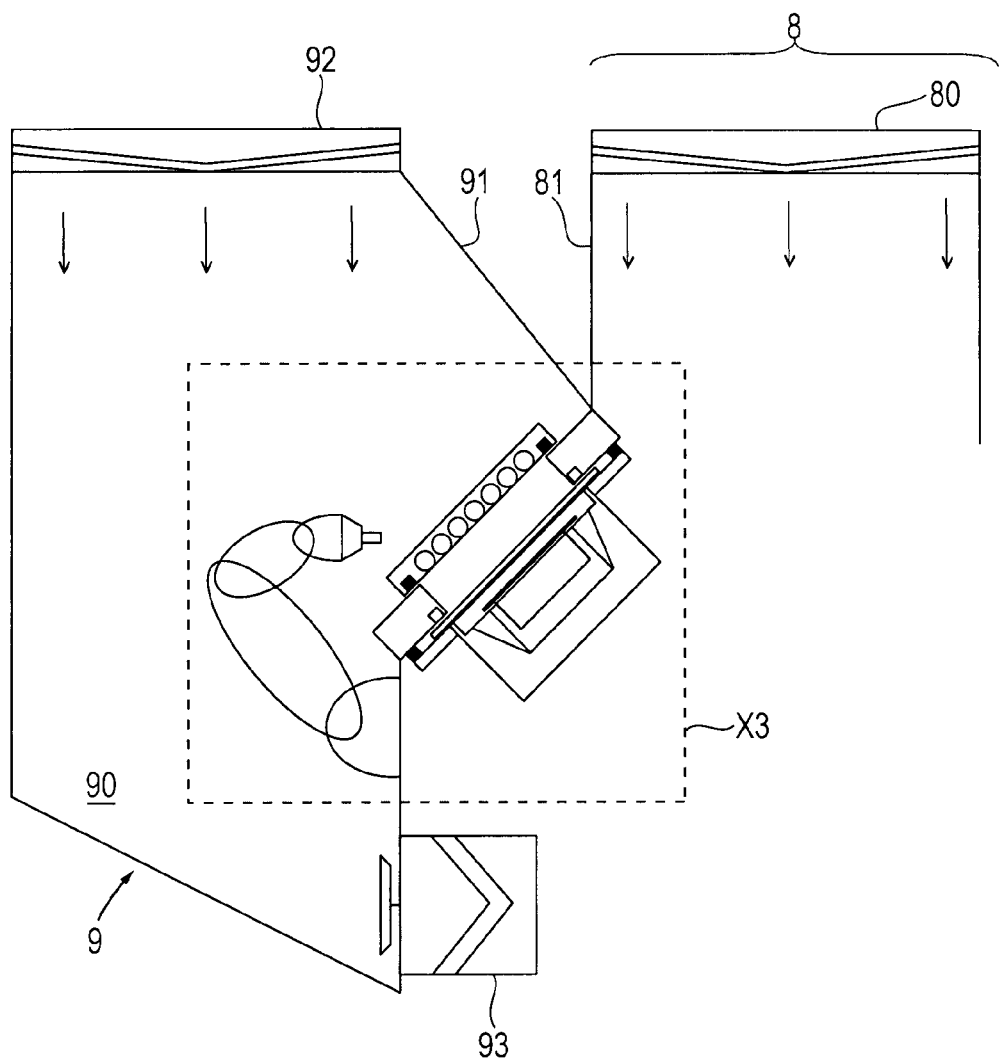
Figure 5B:
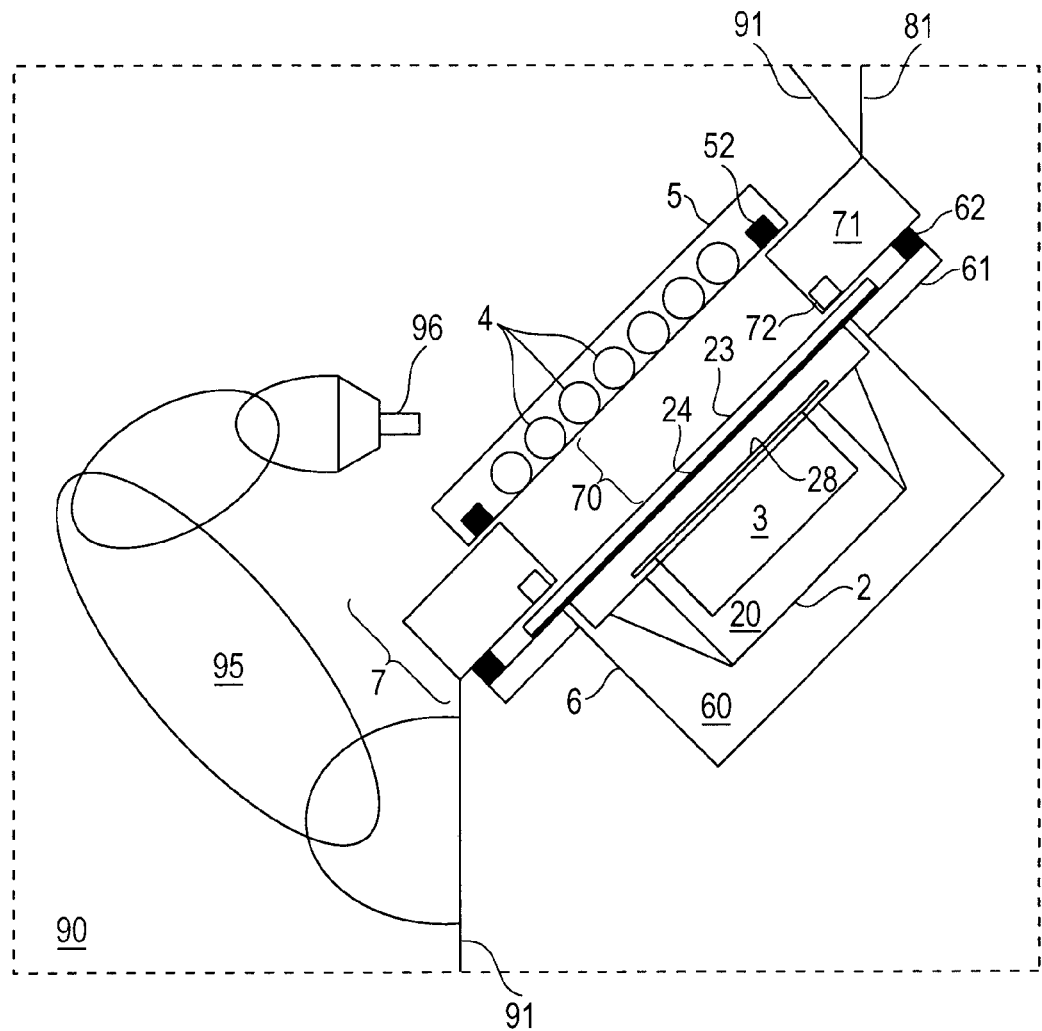
Figure 6A:
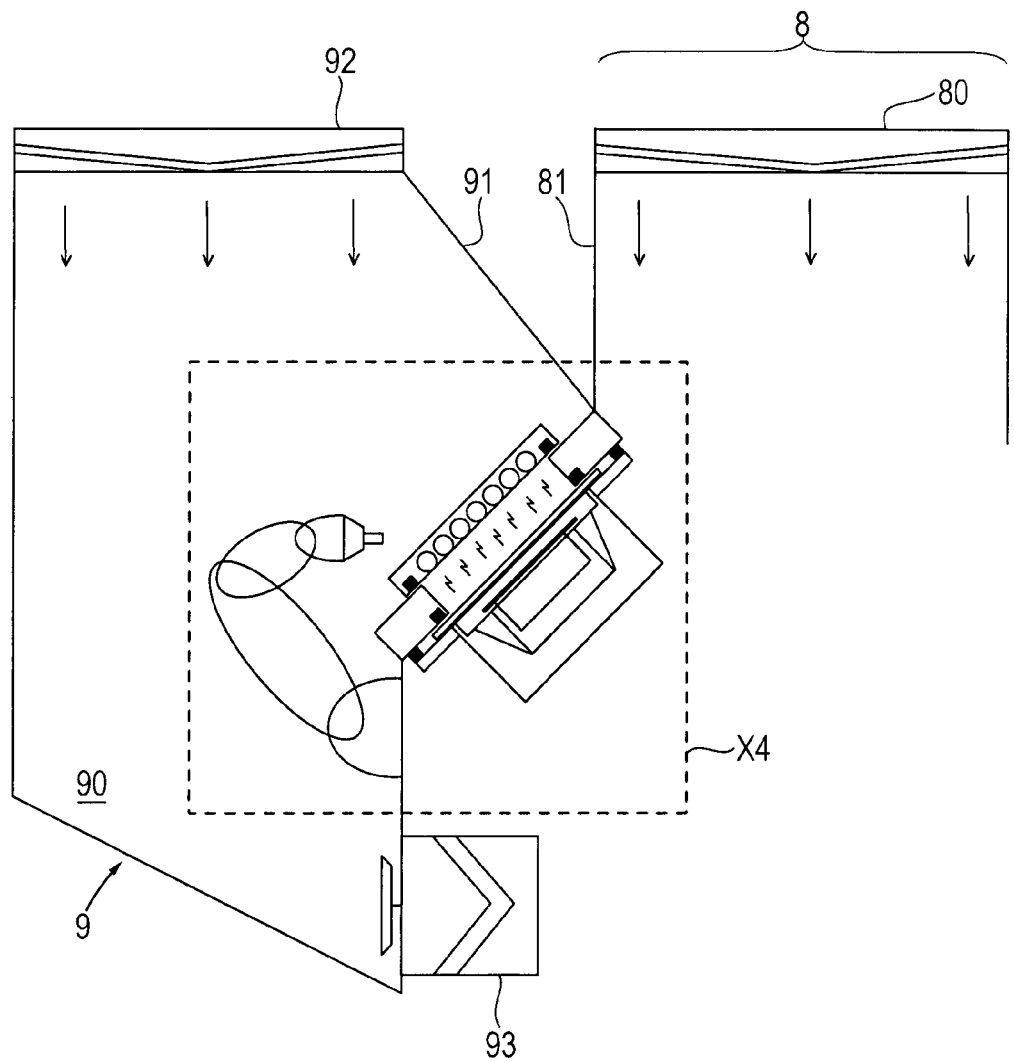
Figure 6B:
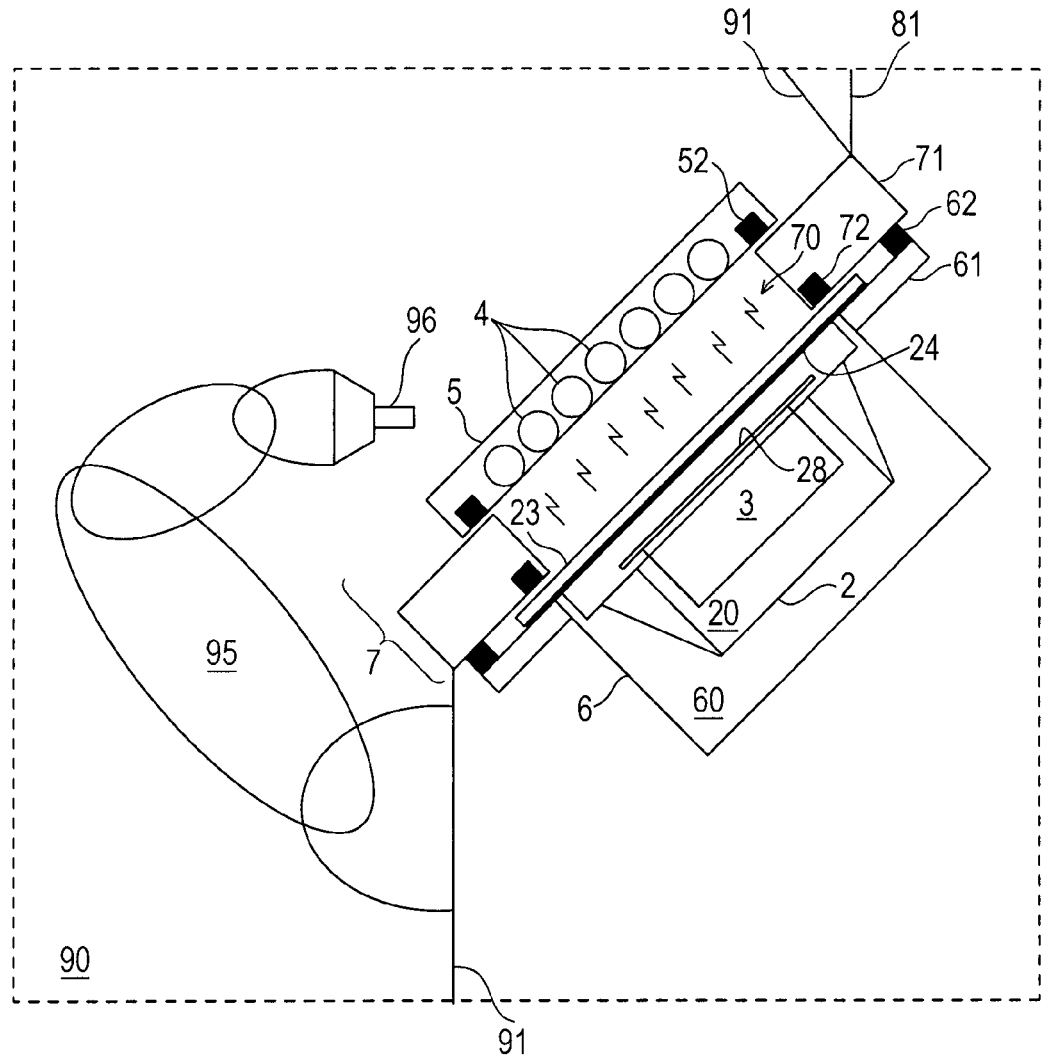
Figure 7A:
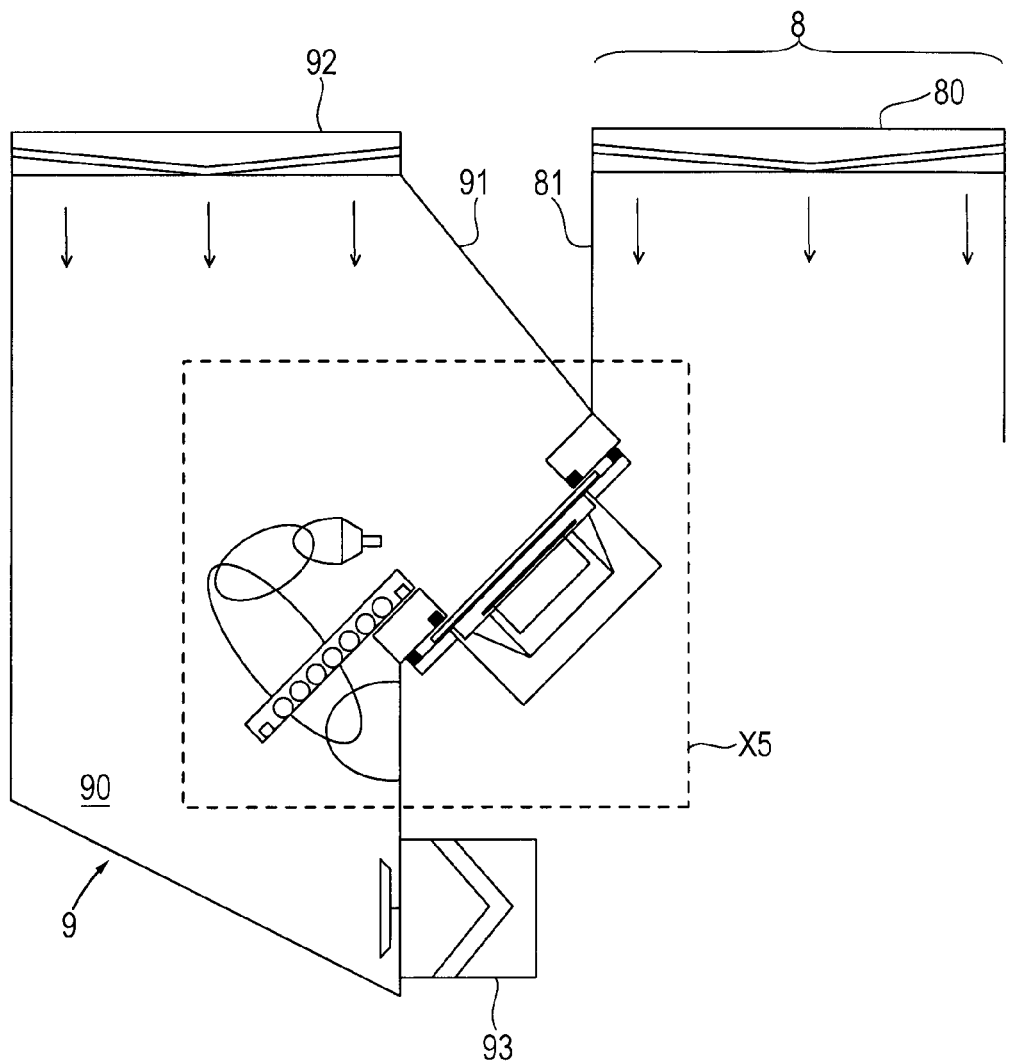
Figure 7B:
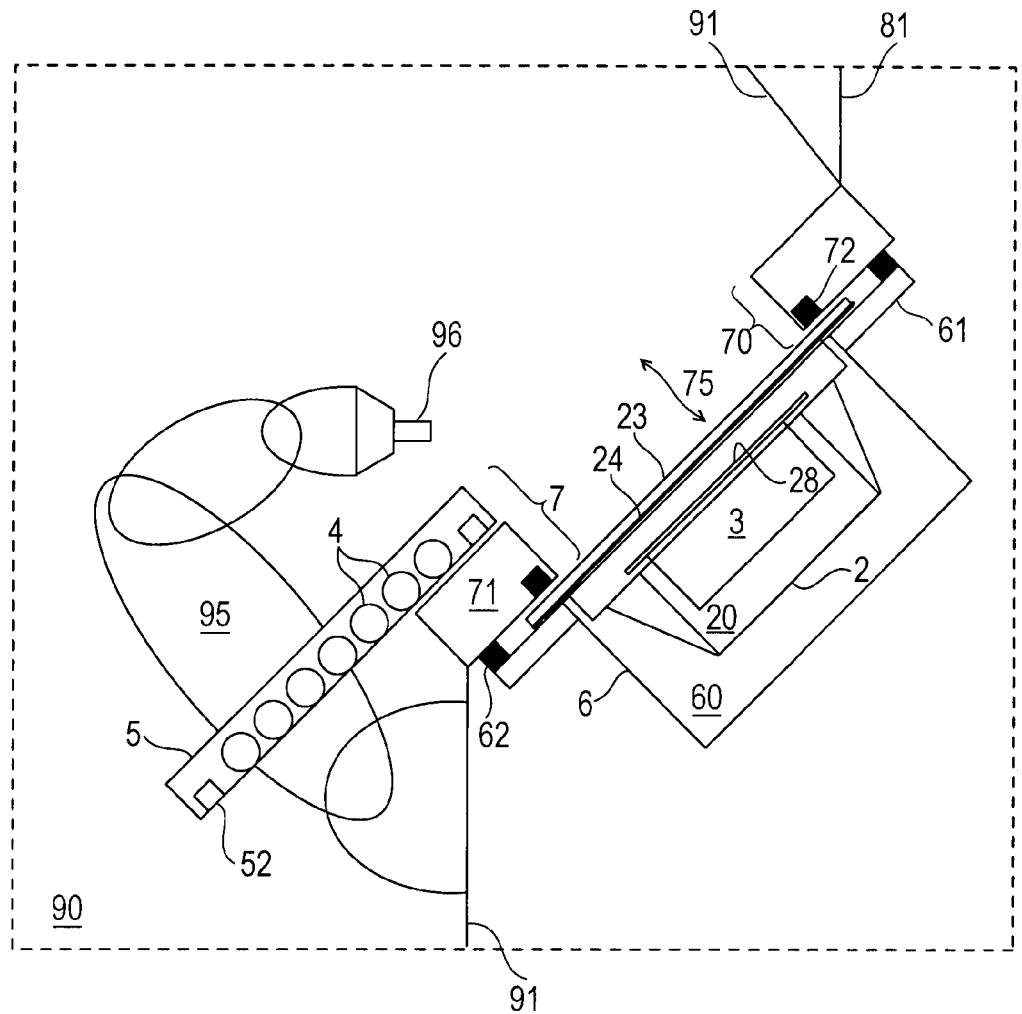
Figure 8A:
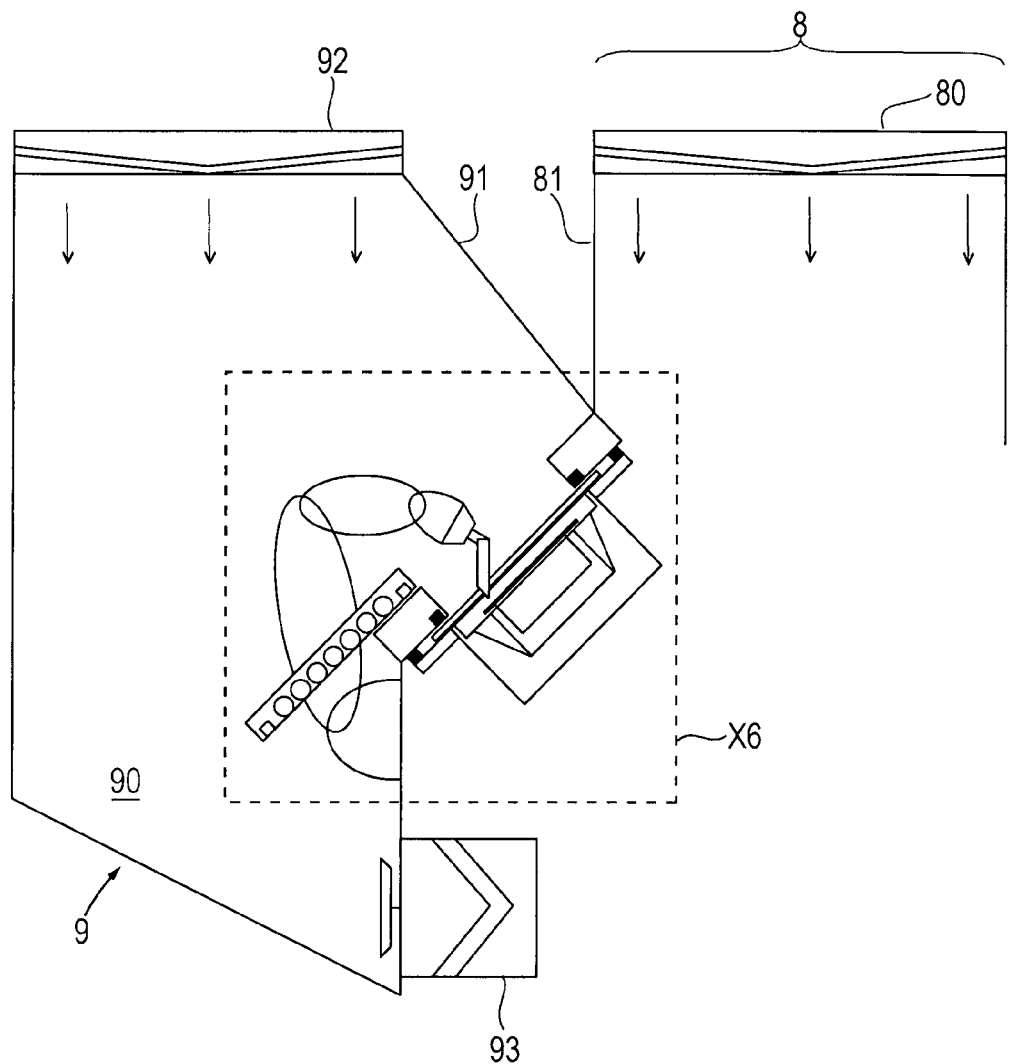
Figure 8B:
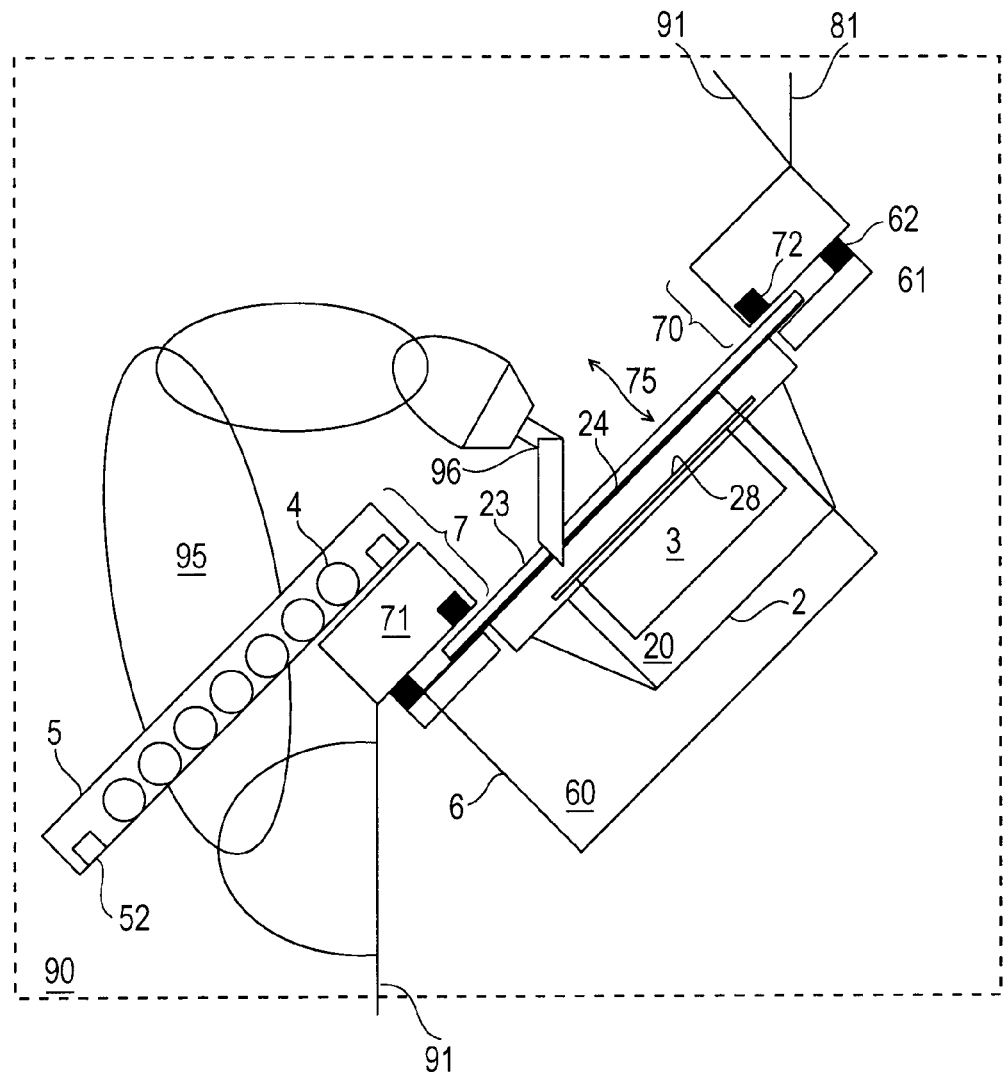
Figure 9A:
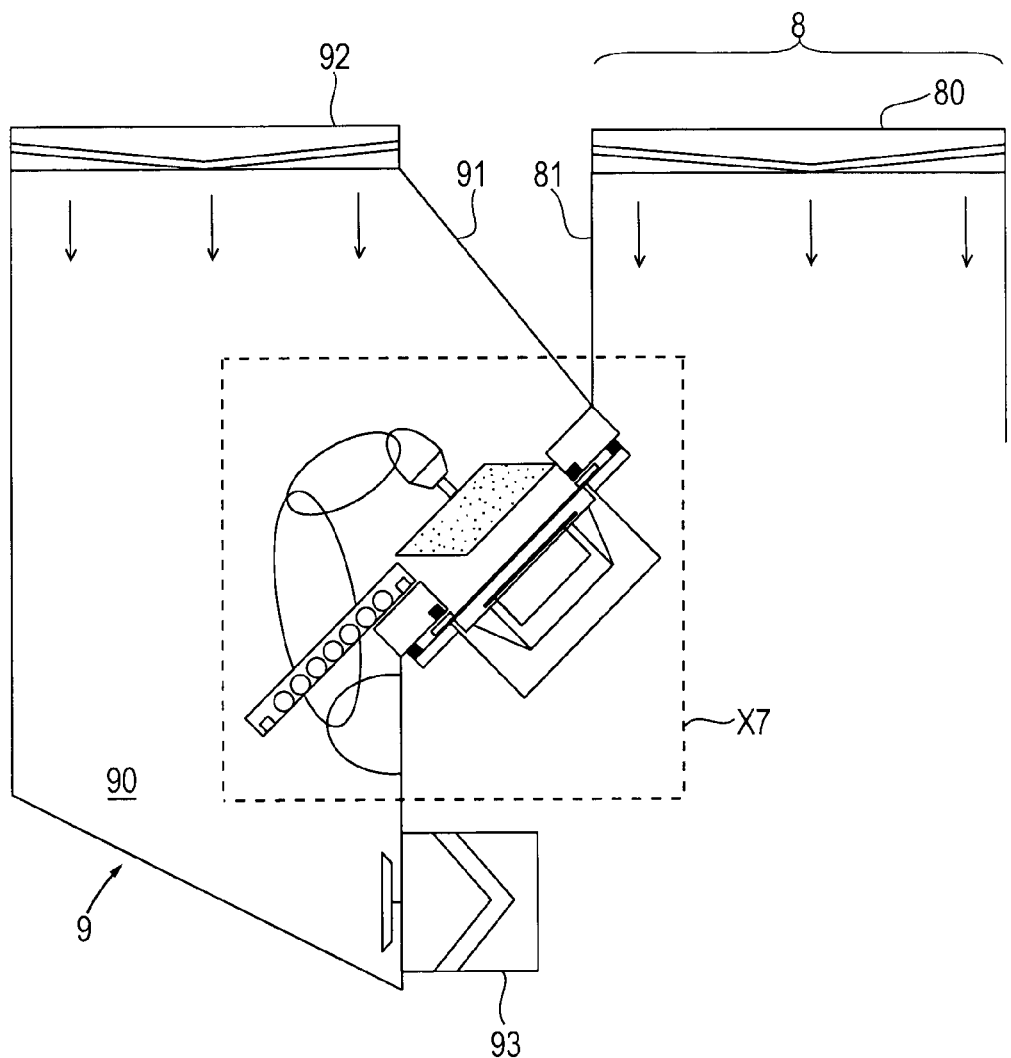
Figure 9B:
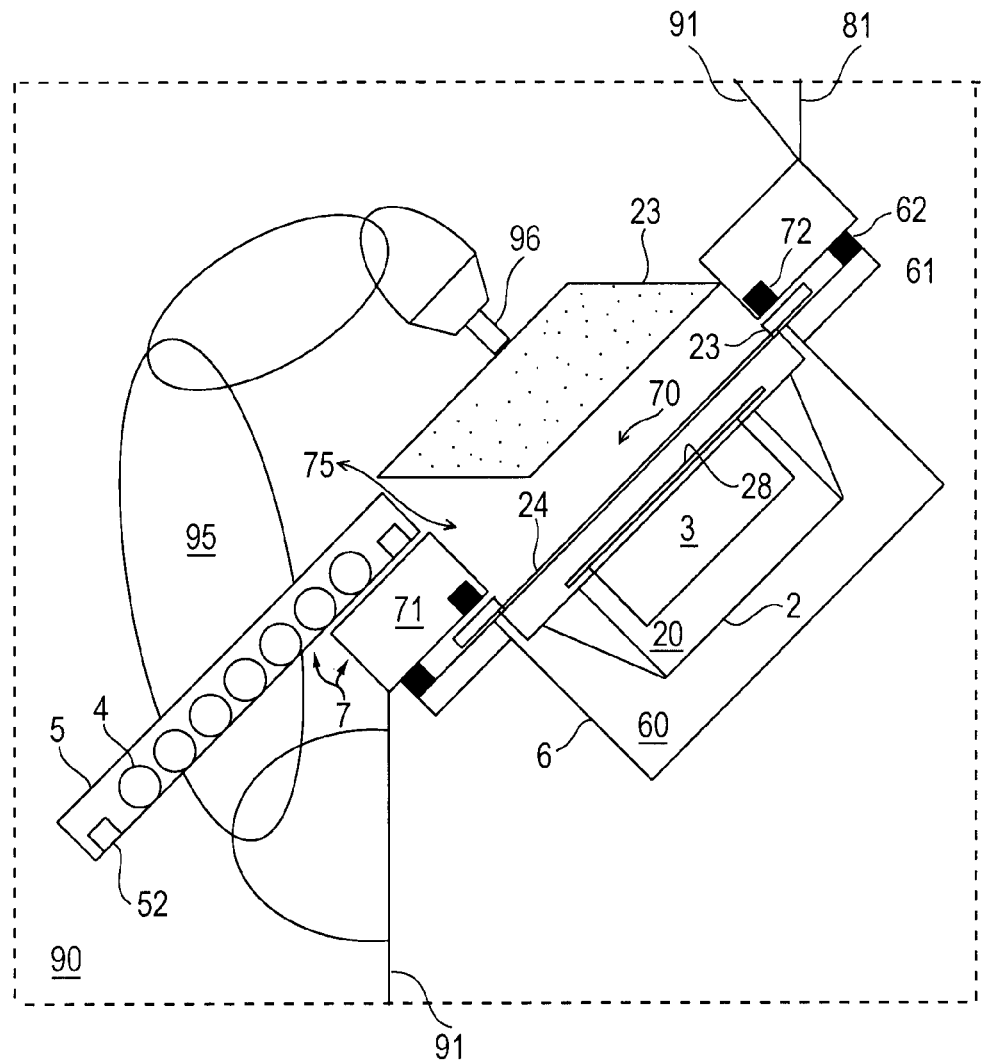
Figure 10A:
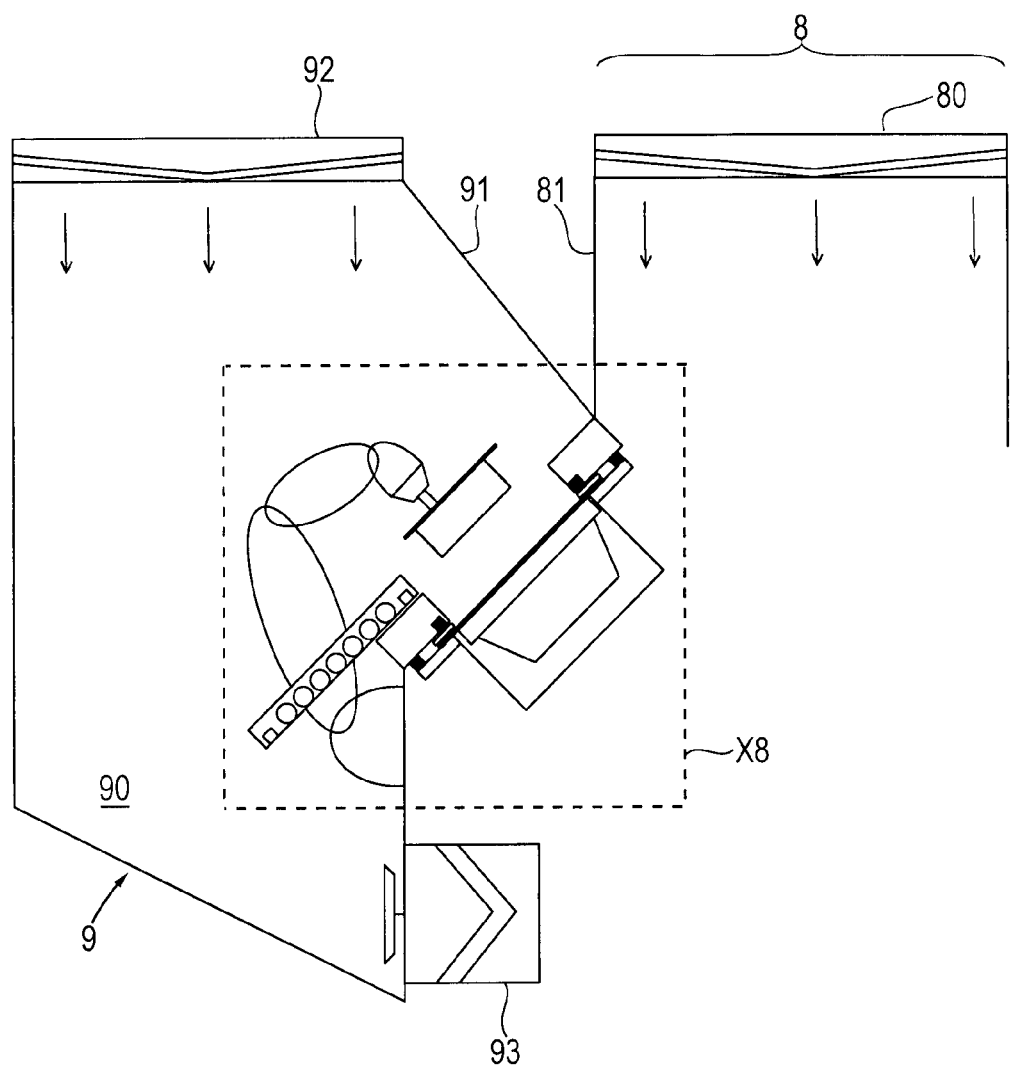
Figure 10B:
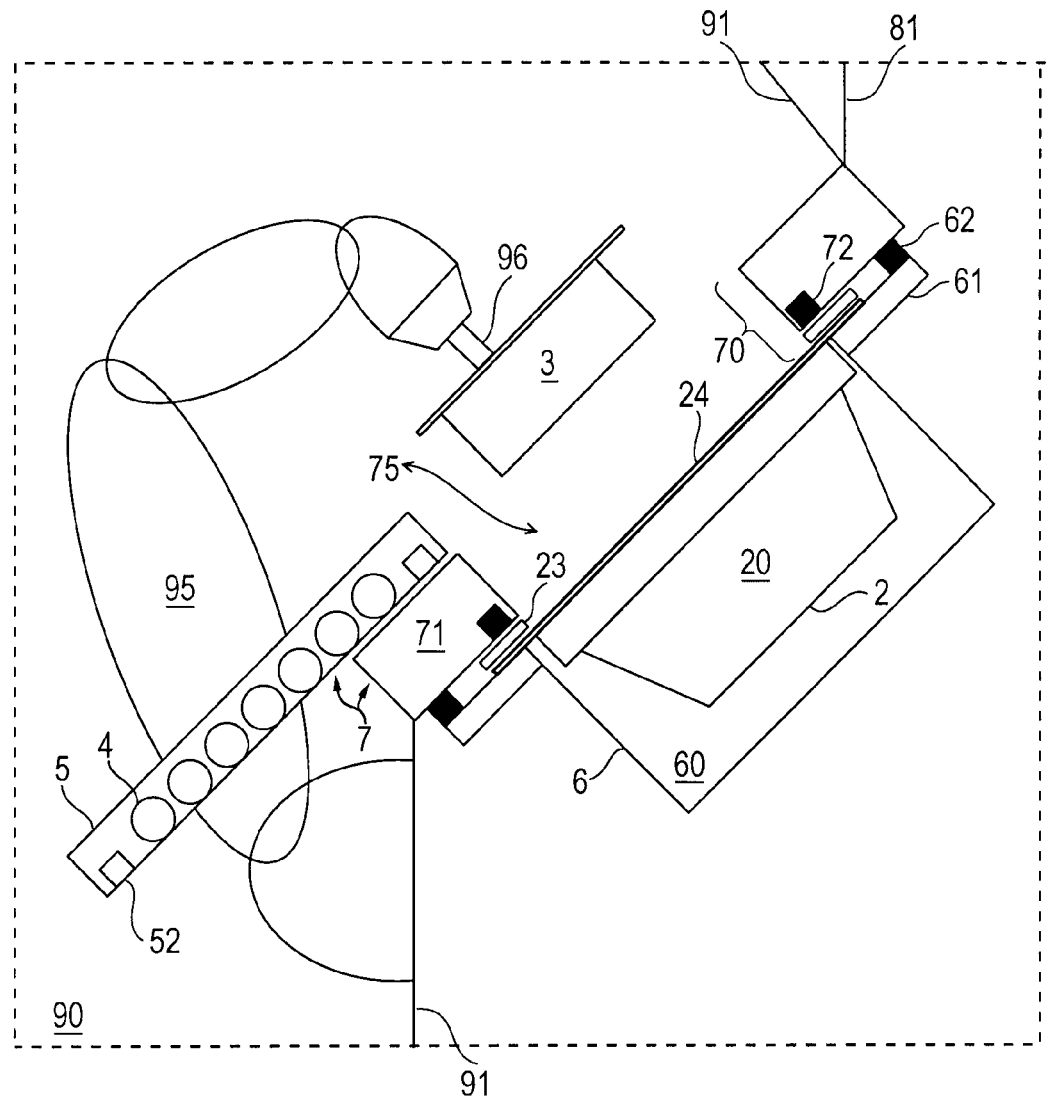

In the drawings:

FIG. 1A—shows a package composed of filled vessel with enclosures, in a transparent perspective view;

FIG. 1B—shows the vessel and the separate enclosures from FIG. 1A, in a perspective view;

FIG. 1C—shows the vessel from FIG. 1A, with an object in the form of a nest for receiving a multiplicity of containers, with a single container, with an inlay and with a cover, in a diagrammatic exploded view;

FIG. 1D—shows the parts as per FIG. 1C, placed one inside the other, in a transparent front view;

FIGS. 2A to 10B: show the arrangement according to the invention for the contamination-free introduction of an object into a containment with portal unit, input station and vessel receptacle, and also the sequence of the process phases, in diagrammatic illustrations;

FIG. 2A—shows process phase 1: removal of the vessel, which has been closed by means of a cover and which contains an object, from the enclosures under controlled clean-room conditions at an input station;

FIG. 2B—shows the enlarged detail X1 from FIG. 2A;

FIG. 3—shows process phase 2: provision of the vessel for introduction, passage into containment closed by door, vessel receptacle empty and detached from portal unit;

FIG. 4A—shows process phase 3: placement of the vessel into vessel receptacle;

FIG. 4B—shows the enlarged detail X2 from FIG. 4A;

FIG. 5A—shows process phase 4: movement of the vessel receptacle into abutment against the portal unit and closure between access flange and flange;

FIG. 5B—shows the enlarged detail X3 from FIG. 5A;

FIG. 6A—shows process phase 5: after a possible integrity test of the object, activation of the decontamination unit;

FIG. 6B—shows the enlarged detail X4 from FIG. 6A;

FIG. 7A—shows process phase 6: switching of the decontamination unit into a passive state, opening of the door, from the side of the containment, open access to the intermediate space as far as the cover;

FIG. 7B—shows the enlarged detail X5 from FIG. 7A;

FIG. 8A—shows process phase 7: transfer apparatus equipped with cutting tool on tool head enters intermediate space, cutting-open of the cover of the vessel;

FIG. 8B—shows the enlarged detail X6 from FIG. 8A;

FIG. 9A—shows process phase 8: transfer apparatus removes cut-away section of the cover and the inlay that may be present;

FIG. 9B—shows the enlarged detail X7 from FIG. 9A;

FIG. 10A—shows process phase 9: transfer apparatus lifts object out of vessel and moves object into working chamber of the containment for further processing; and FIG. 10B—shows the enlarged detail X8 from FIG. 10A.

EXEMPLARY EMBODIMENT

With reference to the appended drawings, the detailed description of the arrangement according to the invention for the contamination-free introduction of a sterile object from a vessel into a containment will be given below, starting with an explanation of the structural design of vessel and object contained therein. Here, the introduction will be discussed on the basis of the illustrated successive sequence of the process phases, such that a description is given of the basic configuration of the arrangement and at the same time of the method steps for introduction performed using the arrangement.

For the entirety of the description that follows, the following statement applies: where reference designations are included in a figure for the purposes of clarity of the drawing, but said reference designations are not discussed in the directly associated text of the description, reference is made to the mention thereof in preceding or subsequent figure descriptions.

FIGS. 1A to 1D

In the delivered state, the vessel 2 situated in a first, outer enclosure 21 and possibly also in an inner, second enclosure 22 forms the package 1. The two enclosures 21,22 are each of bag-like form, are closed, and are preferably provided from a nonwoven fabric or with a nonwoven window. The vessel 2, which is for example of trough-like form and is typically composed of plastic, has, uppermost, a cover 23, normally likewise composed of nonwoven fabric, such as Tyvek®, which is sealed on the vessel edge 24. Alternatively, the cover 23 has a partial surface composed of nonwoven fabric in order to enable gaseous decontaminant to access the object 3 and the containers 30.

In the interior space 20 of the vessel 2, there is situated an encircling support shoulder 25, on which the object 3 accommodated in the interior space 20 is, as it were, suspended, said object being equipped with a multiplicity of containers 30. In the pharmaceutical industry, the term "tub" is common for the vessel 2, and the term "nest" is common for the object 3, whilst the containers 30 are for example in the form of vials or syringes. The object 3 has systematically positioned receiving contours 31, which are of complementary form with respect to the containers 30 and which serve for the ordered arrangement of the containers 30. A sheetlike inlay 28, in turn composed of nonwoven fabric, could lie loosely on top of the object 3. The entire interior of the package 1, that is to say the vessel 2, its interior space 20, the inner surfaces, the bottom side of the cover 23, the inlay 28 and the object 3 and the containers 30, have been made sterile by treatment.

FIGS. 2A to 10B

On the basis of this series of pairs of figures, which illustrate the basic construction of the device and the successive sequence of the process phases 1 to 9 during the introduction, the associated detailed explanatory description will now be given. Here, when discussing the respectively next process phase, only the changes in relation to the preceding process phase will be characterized.

FIGS. 2A and 2B—Construction of the Device and Process Phase 1

In the containment 9, only a fragment of which is illustrated for this explanation, there is situated the working chamber 90 which is surrounded by the wall 91 and above which there is arranged an inlet filter 92 for the feed of a purified air stream into the working chamber 90. The working chamber 90 is equipped with a transfer apparatus 95, which, first and foremost, has a tool head 96. An exhaust-air filter 93 is installed in the lower region of the working chamber 90.

Installed in the wall 91 is a portal unit 7 which has an access flange 71, which access flange has a first seal 72 and borders an intermediate space 70. If not shut off on one side by the closed door 5 and/or on the other side by the vessel receptacle 6 that has been moved into abutment, said intermediate space 70 forms a passage 75 from the outside to the working chamber 90. The door 5 equipped with a second seal 52 is provided within the working chamber 90 and can be moved from a closed position, in which it is set into abutment against the access flange 71, into an open position, in which it has been pivoted into the working chamber 90. The door 5 is simultaneously the support for a decontamination unit 4, preferably by means of UVC radiation. The vessel receptacle 6 is positioned close to the portal unit 7, at the outside on the containment 9, and preferably so as to be pivotable into abutment against the access flange 71, and has the repository 60, accessible through the opening 65, and a flange 61 with the third seal 62 provided thereon.

In a simplified construction, the first seal 72 on the access flange 71 and the second seal 52 on the door 5 may be combined to form one common seal 72/52 arranged on the access flange 71. Such a combined seal 72/52 encompasses the access flange 71 at its inner surfaces facing toward the intermediate space 70, and thus acts at one side between the closed door 5 and the access flange 71 and at the other side between the vessel receptacle 6, which has been pivoted into abutment, and the access flange 71.

Adjoining the containment 9, there is situated the input station 8 with the filter 80 installed at the top and with the side walls 81 for conducting a downwardly flowing air stream generated by the filter 80. The input station 8 allows the removal of the vessel 2, which is closed by means of the cover 23 and contains an object 3, from the enclosures 21,22 under controlled clean-room conditions, and the provision of the vessel 2 for introduction.

In process phase 1, the following situation exists:
  In the input station 8, in the air stream flowing through the filter 80, the enclosures 21,22 are removed from the package 1 under controlled clean-room conditions, and the removed vessel 2 is provided. The sealed cover 23 maintains the sterile state of the object 3 with the containers 30 situated in the interior space 20. The outer surface of the cover 23, however, is no longer guaranteed to be sterile at any rate after the removal from the enclosures 21,22 and as a result of the contact with the atmosphere.
  The door 5 is in the closed position, sealed against the access flange 71 by means of the second seal 52, and the decontamination unit 4 and the transfer apparatus 95 are inactive.
  The vessel receptacle 6 with empty repository 60 has been pivoted away from the access flange 71.
  The passage 75 into the working chamber 90 has been shut off by the closed door 5, and the intermediate space 70 is open to the outside.

FIG. 3—Process Phase 2
  The following situation now exists:
  The entire, now unpacked vessel 2 with the cover 23 which closes it and with the object 3 stored in the vessel 2 is situated, ready for introduction, in the input station 8.

FIGS. 4A and 4B—Process Phase 3
  The following situation now exists:
  The entire vessel 2 has been placed from the input station 8 through the opening 65 into the vessel receptacle 6, which remains pivoted away from the access flange 71.
  Preferably, the vessel edge 24 projects beyond the opening 65, such that the vessel edge 24 is supported on the flange 61, and the vessel 2 is suspended in the repository 60.

FIGS. 5A and 5B—Process Phase 4
  The following situation now exists:
  The vessel receptacle 6 with the vessel 2 accommodated therein has been pivoted into abutment against the access flange 71. Here, the third seal 62 effects the reliable seal between flange 61 and access flange 71, and the first seal 72 effects the reliable seal between flange 61 and vessel edge 24, or the preferably sealed cover 23 thereon.
  The passage 75 into the working chamber 90 remains shut off by the closed door 5, but now also to the outside by the vessel receptacle 6 that has been pivoted into abutment, such that the intermediate space 70 is now hermetically insulated on all sides.
  The content of the vessel 2 may be subjected to an integrity test in order to identify, before the process is continued, that the content satisfies the cleanliness requirement.
  The first seal 72 is activated.

FIGS. 6A and 6B—Process Phase 5
  The following situation now exists:
  The decontamination unit 4 is brought into a state of action in order to make the intermediate space 70, all surfaces facing toward this, that is to say the inner annular surface of the intermediate flange 71, the outer surface of the cover 23 and the possible free surface on the first seal 72, sterile.

FIGS. 7A and 7B—Process Phase 6

The following situation now exists:

The decontamination unit 4 is deactivated or is retracted while remaining in an activated state.

The door 5 is opened by movement into the interior of the working chamber 90, such that the passage 75 into the intermediate space 70 as far as the cover 23 is accessible from the interior of the working chamber 90.

FIGS. 8A and 8B—Process Phase 7

The following situation now exists:

The cutting tool on the tool head 96 of the transfer apparatus 95 is brought into use and pivots toward the intermediate space 70 in order to cut away the cover 23 in order to enable the object 3 to be removed from the vessel 2.

FIGS. 9A and 9B—Process Phase 8

The following situation now exists:

The gripping tool on the tool head 96 of the transfer apparatus 95 is brought into use in order to move the cut-away cover 23 and possibly also the inlay 28 lying on top of the object 3 into the interior of the working chamber 90.

FIGS. 10A and 10B—Process Phase 9

The following situation now exists:

By means of the gripping tool on the tool head 96 of the transfer apparatus 95, the object 3 is gripped, lifted out of the vessel 2 and moved into the working chamber 90.

The object 3 with the containers 30 stored therein is supplied to the further processing operation in the containment 9.

The empty object 3 can be placed back into the vessel 2.

The arrangement is brought into the process phase 1 or 2, that is to say the door 5 is moved into the closed position and is thus sealed against the access flange 71 again. The vessel receptacle 6 is pivoted away from the access flange 71 in order for the vessel 2, which is now empty or laden with the empty object 3, to be removed from the vessel receptacle 6.

The invention claimed is:

1. A method for the contamination-free introduction of a sterile object (3) with containers (30) stored therein from a vessel (2) into a containment (9) using an arrangement comprising:
   a) a portal unit (7) having:
   aa) an access flange (71) which is arranged in the wall (91) and which forms a passage (75) from the outside into a working chamber (90); and
   ab) a door (5) which sealingly closes the passage (75) and which, in order to be opened, can be moved into the working chamber (90); and
   b) a vessel receptacle (6) having:
   ba) a repository (60) for holding a vessel (2) that has been introduced into the vessel receptacle (6);
   bb) an opening (65) for the introduction of the vessel (2) into the repository (60); and
   bc) a flange (61) for interacting with the access flange (71), wherein c) a decontamination unit (4) is designed to, when the door (5) has been closed, the vessel receptacle (6) has been docked to the access flange (71) and the vessel (2) has been stored in the vessel receptacle (6), decontaminate an outer surface, facing toward the door (5), of the cover (23),
   the method comprising the following sequence of process phases:

a) removing the vessel (2), which has been closed by means of a cover (23) and which contains an object (3), from enclosures (21,22) under controlled clean-room conditions at an input station (8);
   b) providing the respectively individual vessel (2), which has been closed by means of the cover (23) and which has the sterile object (3) stored therein, for contamination-free introduction into a working chamber (90) of a containment (9); here:
   the passage (75) to the working chamber (90) is outwardly open but the passage (75) into the containment (9) is closed by the door (5), the decontamination unit (4) is inactive, the repository (60) of the vessel receptacle (6) is open and empty, and the vessel receptacle (6) is detached from the portal unit (7);
   c) placing the provided individual vessel (2) into the repository (60); here:
   it remains the case that the passage (75) is outwardly open but the passage (75) into the containment (9) is closed by the door (5), the decontamination unit (4) is inactive and the vessel receptacle (6) is detached from the portal unit (7), but now the repository (60) is filled with a vessel (2);
   d) moving the vessel receptacle (6) into abutment against the portal unit (7); here:
   the access flange (71) of the portal unit (7) and the flange (61) are sealed against one another;
   furthermore, the passage (75) into the containment (9) is closed by the door (5),
   the decontamination unit (4) is inactive and the repository (60) is filled with a vessel (2); and—the passage (75) is also outwardly closed, specifically by the vessel receptacle (6) docked in a sealed manner to the portal unit (7);
   e) activating the decontamination unit (4) to bring the latter into a state of action;
   here:—it remains the case that the access flange (71) of the portal unit (7) and the flange (61) are sealed against one another, the passage (75) into the containment (9) is closed by the door (5), the repository (60) is filled with a vessel (2), and the passage (75) is also outwardly closed, specifically by the vessel receptacle (6) docked in a sealed manner to the portal unit (7);
   and now—the outer surface, exposed to the door (5), of the cover (23) and the intermediate space (70) and all surfaces facing toward this are made sterile; f) deactivating the decontamination unit (4) to bring the latter out of a state of action, an opening the door (5); here:
   it remains the case that the access flange (71) of the portal unit (7) and the flange (61) are sealed against one another, the repository (60) is filled with a vessel (2), the passage (75) is outwardly closed, specifically by the vessel receptacle (6) docked in a sealed manner to the portal unit (7), and the outer surface of the cover (23), the intermediate space (70) and all surfaces facing toward this are sterile; and now—the passage (75) into the containment (9) is open;
   g) cutting open the cover (23) of the vessel (2); here:
   it remains the case that the access flange (71) of the portal unit (7) and the flange (61) are sealed against one another, the repository (60) is filled with a vessel (2), the passage (75) is outwardly closed, specifically by the vessel receptacle (6) docked in a sealed manner to the portal unit (7), the outer surface of the cover (23), the intermediate space (70) and all surfaces facing toward this are sterile, and the passage

(75) into the containment (9) is open; and now—the access to the object (3) situated in the vessel (2) is open;

h) removing the object (3) from the vessel (2) and transferring the object (3) into the working chamber (90) of the containment (9) for further processing; here:
it remains the case that the access flange (71) of the portal unit (7) and the flange (61) are sealed against one another, the passage (75) is outwardly closed, specifically by the vessel receptacle (6) docked in a sealed manner to the portal unit (7), and the passage (75) into the containment (9) is open; and—now the repository (60) is now filled only with the empty vessel (2); and i) returning the arrangement into the starting phase, that is to say moving the door (5) into the closed position, which is thus sealed against the access flange (71) again, pivoting the vessel receptacle (6) away from the access flange (71), and removing the empty vessel (2) from the repository (60).

2. The method as claimed in claim 1, wherein:
a) after the vessel receptacle (6) with the vessel (2) that has been placed in the repository (60) has been moved into abutment against the portal unit (7) and before the decontamination unit (4) is activated or brought into its state of action, the object (3) is subjected to an integrity test in order to identify whether the content of the vessel (2) satisfies a cleanliness requirement; wherein,
b) if the integrity test yields a negative result, the vessel receptacle (6) is pivoted away from the portal unit (7) in order for the, in effect, defective vessel (2) to be removed from the repository (60).

3. The method as claimed in claim 2, wherein the cutting-open of the cover (23) of the vessel (2), the removal of the object (3) from the vessel (2) and the transfer of the object (3) with the containers (30) stored therein into the working chamber (90) of the containment (9) are performed by means of the transfer apparatus (95) positioned in the working chamber (90).

4. The method as claimed in claim 3, wherein a cut-away part of the cover (23) is moved into the working chamber (90) by means of the transfer apparatus (95) positioned in the working chamber (90).

5. The method as claimed in claim 1, wherein:
a) the individual vessel (2) which has been closed by means of the cover (23) is, together with its sterile content, specifically the object (3) stored in the vessel (2) and the containers (30) accommodated in said object (3), provided with at least one enclosure (21,22) and thus, in the delivered state, forms a package (1); and
b) the provision of the individual vessel (2) before it is placed into the vessel receptacle (6) is performed, in an input station (8) belonging to the arrangement, as a release of the vessel (2) from the respective package (1) under controlled clean-room conditions.

6. A method for the contamination-free introduction of a sterile object with containers stored therein from a vessel into a containment using the arrangement as claimed in claim 1, comprising the following sequence of process phases:
a) removing the vessel, which has been closed by means of a cover and which contains an object, from enclosures under controlled clean-room conditions at an input station;
b) providing the respectively individual vessel, which has been closed by means of the cover and which has the sterile object stored therein, for contamination-free introduction into a working chamber of a containment; here:
the passage to the working chamber is outwardly open but the passage into the containment is closed by the door, the decontamination unit is inactive, the repository of the vessel receptacle is open and empty, and the vessel receptacle is detached from the portal unit;

c) placing the provided individual vessel into the repository; here:
it remains the case that the passage is outwardly open but the passage into the containment is closed by the door, the decontamination unit is inactive and the vessel receptacle is detached from the portal unit, but now the repository is filled with a vessel;

d) moving the vessel receptacle into abutment against the portal unit; here:
the access flange of the portal unit and the flange are sealed against one another;
furthermore, the passage into the containment is closed by the door, the decontamination unit is inactive and the repository is filled with a vessel; and
the passage is also outwardly closed, specifically by the vessel receptacle (6) docked in a sealed manner to the portal unit;

e) activating the decontamination unit to bring the latter into a state of action; here:
it remains the case that the access flange of the portal unit and the flange are sealed against one another, the passage into the containment is closed by the door, the repository is filled with a vessel, and the passage is also outwardly closed, specifically by the vessel receptacle docked in a sealed manner to the portal unit; and now
the outer surface, exposed to the door, of the cover and the intermediate space and all surfaces facing toward this are made sterile;

f) deactivating the decontamination unit to bring the latter out of a state of action, an opening the door; here:
it remains the case that the access flange of the portal unit and the flange are sealed against one another, the repository is filled with a vessel, the passage is outwardly closed, specifically by the vessel receptacle docked in a sealed manner to the portal unit, and the outer surface of the cover, the intermediate space and all surfaces facing toward this are sterile; and now
the passage into the containment is open;

g) cutting open the cover of the vessel; here:
it remains the case that the access flange of the portal unit and the flange are sealed against one another, the repository is filled with a vessel, the passage is outwardly closed, specifically by the vessel receptacle docked in a sealed manner to the portal unit, the outer surface of the cover, the intermediate space and all surfaces facing toward this are sterile, and the passage into the containment is open; and now
the access to the object situated in the vessel is open;

h) removing the object from the vessel and transferring the object with the containers stored therein into the working chamber of the containment for further processing; here:
it remains the case that the access flange of the portal unit and the flange are sealed against one another, the passage is outwardly closed, specifically by the vessel receptacle docked in a sealed manner to the portal unit, and the passage into the containment is open; and now the repository is now filled only with the empty vessel; and i) returning the arrangement into the starting phase, that is to say moving the door into the closed position, which is thus sealed against the access flange again, pivoting the vessel receptacle away from the access flange, and removing the empty vessel from the repository;

and wherein:

j) after the vessel receptacle with the vessel that has been placed in the repository has been moved into abutment against the portal unit and before the decontamination unit is activated or brought into its state of action, the object is subjected to an integrity test in order to identify whether the content of the vessel satisfies a cleanliness requirement; wherein, k) if the integrity test yields a negative result, the vessel receptacle is pivoted away from the portal unit in order for the, in effect, defective vessel to be removed from the repository.

7. The method as claimed in claim 6, wherein the cutting-open of the cover of the vessel, the removal of the object from the vessel and the transfer of the object with the containers stored therein into the working chamber of the containment are performed by means of the transfer apparatus positioned in the working chamber.

8. The method as claimed in claim 7, wherein a cut-away part of the cover is moved into the working chamber by means of the transfer apparatus positioned in the working chamber.

9. The method as claimed in claim 6, wherein:

a) the individual vessel which has been closed by means of the cover is, together with its sterile content, specifically the object stored in the vessel and the containers accommodated in said object, provided with at least one enclosure and thus, in the delivered state, forms a package; and b) the provision of the individual vessel before it is placed into the vessel receptacle is performed, in an input station belonging to the arrangement, as a release of the vessel from the respective package under controlled clean-room conditions.

\* \* \* \* \*